United States Patent [19]

Rosenberg et al.

[11] Patent Number: 4,976,951
[45] Date of Patent: Dec. 11, 1990

[54] DENTAL CARIES DIAGNOSTIC AND LOCALIZATION TECHNIQUE

[76] Inventors: Melvyn Rosenberg, 12 Yeda Am, Ramat Gan 52526; Ilana Eli, 26 Shazar, Ramat Gan 52247; Ervin Weiss, 9 Lipsky, Tel-Aviv 62195, all of Israel

[21] Appl. No.: 770,201

[22] Filed: Aug. 28, 1985

[51] Int. Cl.$^5$ .................. A61K 49/00; C12Q 1/00; C12Q 1/24; C12Q 1/04
[52] U.S. Cl. .................. 424/7.1; 424/2; 435/4; 435/7; 435/30; 435/34; 435/36
[58] Field of Search ............ 424/7.1, 9; 435/4, 7, 435/36, 30, 34; 514/781; 433/215, 168.1, 213; 378/62; 264/16–20; 106/38.2

[56] References Cited

U.S. PATENT DOCUMENTS

| | | | |
|---|---|---|---|
| 3,279,068 | 10/1966 | Stark | 424/7.1 |
| 3,309,274 | 3/1967 | Brilliant | 424/9 |
| 3,890,200 | 6/1975 | Jordan et al. | 195/103.5 R |
| 3,903,252 | 9/1975 | Stearns et al. | 424/7.1 |
| 4,359,455 | 11/1982 | Nakamura et al. | 424/7.1 |
| 4,368,272 | 1/1983 | Kashket . | |

OTHER PUBLICATIONS

Stanier, R. Y., Adelberg, E. A. and Ingrahm, John L., The Microbial World (Prentice-Hall, Englewood Cliffs, N.J.), 1976.
Lennette, E. H. (ed.) Manual of Clinical Microbiology, American Soc. Microbiology, Washington, D.C. (1985), p. 1058.
Winklers, S.: Essentials of Complete Denture Prosthodontics, W. B. Saunders Co., (1979), pp. 141–170.

*Primary Examiner*—Douglas W. Robinson
*Attorney, Agent, or Firm*—Benjamin J. Barish

[57] ABSTRACT

A method for detecting and localizing bacterial growth on a surface comprising the steps of:
(a) applying a solid substrate to the surface;
(b) removing said substrate from said surface and incubating said substrate for purposes of facilitating ultimate visualization of selective bacterial growth; and
(c) observing the locus of bacterial growth on the substrate.

The method is particularly effective in detecting and localizing cariogenic activity in the mouth.

19 Claims, No Drawings

DENTAL CARIES DIAGNOSTIC AND LOCALIZATION TECHNIQUE

BACKGROUND OF THE INVENTION

1. Field of the Invention

The invention relates to a method and apparatus for the early diagnosis and localization of dental caries.

2. Description of Relevant Materials and Background

Until recently, there was little reason to be concerned with attempting to localize the development of dental caries, other than from a theoretical viewpoint. Practically speaking, no techniques were available to arrest the development of dental caries and early information as to their existance was of little practical use.

Recently however, developments in dental science such as the use of polymeric sealants have made it possible to arrest the growth and development of dental caries such that it is now of considerable practical interest to be able to determine and localize the early presence of dental caries so that their further development may be arrested.

Traditional examination techniques such as x-rays and examination with a dental explorer are capable of detecting the presence of dental caries only at relatively late stages of development when the development can no longer be arrested by newly developed techniques. Furthermore, the use of such techniques on a regular basis is limited because of the health dangers associated with radiation, as well as the discomfort, and possible damage to the patient since it has been shown that probing with an explorer damages the dentine in incipient caries. Furthermore, performance of such techniques requires trained personnel and does not allow for detection by the patient himself, for example.

It would, therefore, be very desirable to provide a technique which allows for the early detection and localization of dental caries by a procedure which is simple to perform, even by untrained personnel, and which is not disturbing to the patient, as has traditionally been the case.

Although techniques have now been developed which yield a general measure of cariogenic microorganism activity in the mouth, none of the available techniques actually localizes the site of the cariogenic activity.

STARK, U.S. Pat. No. 3,279,068, discloses a method of detecting carious tissue and dental calculus. The patent discloses that 9-aminoacridine and its hydrochloride are unique agents for disclosing the presence of dental caries and calculus. The patent does not discuss the detection of Streptococcus mutans (S. mutans) or other cariogenic microorganisms.

GREEN, U.S. Pat. No. 3,332,743, discloses a diagnostic test for dental caries activity. The test gives a color response at room temperature, based on the sum total of metabolic activity of the saliva (column 1, line 60). In accordance with that test, a buffered substrate solution containing a suitable indicator dye measures the oxidation rate of a saliva specimen by measuring the time period in which the indicator dye undergoes a distinct color change, which is taken as a measure of dental caries activity (column 1, line 70). The test does not provide spatial localization of microorganisms associated with the cariogenic activity.

HOERMAN et al., U.S. Pat. No. 3,746,625, discuss a 48-hour test for S. mutans in plaque. The method involves removing a series of specimens from the patient's mouth, generally by insertion of dental floss between the teeth to remove material in the mouth adjacent to the tooth (column 1, line 60).

The floss with the specimen on it is dropped into a test solution. After a 48-hour period, a yellow color indicates the presence of S. mutans (column 1, line 65 and column 2, line 15).

There is no disclosure of localizing cariogenic activity to a specific area of a tooth. Moreover, dental floss, when inserted between two teeth will naturally sample one surface of each tooth at the same time. Additionally, since cariogenic activity is not limited to S. mutans, a test limited to this analyte may not be completely accurate.

STEARNS et al., U.S. Pat. No. 3,903,252, describes a dental disclosing composition to be used in the mouth. A staining agent associated with the composition adheres to plaque on the teeth. However, the presence of plaque on the teeth does not necessarily indicate the presence of microorganisms which cause cariogenic activity. Thus, dental disclosing compositions, as exemplified by this patent, do not localize cariogenic activity.

NAKAMURA et al., U.S. Pat. No. 4,359,455, disclose a diagnostic test composition for dental caries activity. The composition contains a saccharide as a carbon source for promoting the acid-producing capacity of bacteria in the mouth as well as a pH indicator which has a color change point at a pH range of 5 to 7. According to the method, a sample of dental plaque is collected and introduced into the composition, and then the change of color of the pH indicator contained in the composition is observed with the naked eye (column 1, line 52). Thus, the composition constitutes an overall measure of bacterial activity in the mouth, and is not intended to localize the activity.

DEYLOFF, U.S. Pat. No. 4,468,456, discloses a medium for differentiating S. mutans. The patent contemplates the innoculation of a culture medium with samples taken from the mouth (column 6, line 30). There is no disclosure showing the localization of cariogenic activity to specific areas of the teeth.

SUMMARY OF THE INVENTION

It is, therefore, an object of the invention to provide a technique for determining the extent and location of cariogenic activity in a manner which can be performed by untrained personnel at no risk, or discomfort to the patient.

According to the present invention, there is provided a method for detecting the presence, extent and location of one or more specified microorganisms on a surface, such as on a person's teeth or in another medium, comprising: (a) contacting the surface with a solid substrate containing at least one substance essential for the growth of the specified microorganism; (b) removing the solid substrate from the surface and immersing it in a liquid growth medium lacking said at least one substance essential for the growth of the specified microorganism but otherwise having the necessary growth ingredients for growing the specified microorganism; and (c) incubating the liquid growth medium with the solid substrate immersed therein to promote the growth of the specified microorganism at the interface between the solid substrate and the liquid medium.

The invention also provides, for use in detecting the presence, extent and location of a specified microorganism in an examined medium, the combination comprising: a solid substrate containing at least one substance essential for the growth of the specified microorganism; and a liquid growth medium lacking said at least one substance essential for the growth of the specified microorganism but otherwise having the necessary growth ingredients for growing the specified microorganism, such that by effecting contact between the examined medium and the solid substrate, immersing the solid substrate into the liquid growth medium, and then incubating the liquid growth medium with the solid substrate immersed therein, the growth of the specified microorganism is promoted at the interface between the solid substrate and the liquid growth medium.

The invention is particularly applicable wherein the examined medium containing the one or more specified microorganisms to be detected is the surface of a subject's teeth, or wherein the solid substrate would preferably be an impressionable material, such as chewing gum, applied to the subject's teeth.

An important feature of the method of the present invention is that it uses a liquid rather than a gel as the growth medium. This enables the method to be conveniently performed by non-professional personnel, even by the patient himself, at no risk or discomfort to the patient.

According to the preferred embodiments of the invention described below, the liquid growth medium includes an indicator substance which becomes associated with the microorganism during the incubation of the substrate in the liquid growth medium to facilitate identification of the specified microorganism; in addition, the substrate, or the liquid growth medium, may also contain at least one substance which inhibits the growth of microorganisms except the specified microorganism. One possible essential substance absent from the solid substrate and present in the liquid is a carbon source such as sucrose, for example. Other substances for the growth of the microorganism which may be present in the liquid comprise: other sugars (as carbon sources), amino acids (carbon, nitrogen and sulphur sources), sulphate ions, phosphate ions, etc.

The technique is most preferably utilized to localize cariogenic activity on a tooth surface. In this embodiment the substrate may be selected from the group consisting of: chewing gum, plant or vegetable gum, alginate, a paper card, a plaster mold, wax, silicone, cellophane, etc.

As noted above, the substrate or liquid growth medium may further, or alternatively, comprise an antibacterial agent to prevent growth of bacteria other than the bacteria of interest. For example, 60% sucrose is inhibitory to noncariogenic microorganisms as well as being a main carbon source.

When utilized in the mouth the technique most preferably involves:
(a) contacting the mouth interior with a substrate in a manner whereby suspected bacteria within the mouth come into direct contact with the substrate, the substrate comprising at least one carbon source important for the growth of the bacteria on the substrate;
(b) removing the substrate from the mouth and incubating the substrate within a liquid medium comprising all additional substances within a liquid medium comprising all additional substances for the growth of the suspected bacteria on the substrate for a sufficient period of time to allow for the growth of the bacteria on the substrate in a manner whereby the locus of bacteria on the substrate is not substantially disturbed upon exposure to the liquid medium; and
(c) observing the growth of the bacteria on the substrate to identify the presence and locus of cariogenic activity in the mouth.

Under certain circumstances it may be necessary to rinse the substrate prior to incubating it.

The liquid medium includes a disclosing agent such as a dye, in one embodiment, such as gentian violet, trypan blue, potassium tellurite, or mixtures thereof, for example, to facilitate visualization of the bacteriological activity.

According to another embodiment, a chromogenic immunoassay system may be utilized; that is, the disclosing agent may be an immune serum containing antibodies to be bound to the bacterium during incubation of the substrate. The antibodies may be labelled to facilitate observation, or may in turn be unlabelled for subsequent coupling with an enzyme-anti-immunoglobulin conjugate.

DESCRIPTION OF PREFERRED EMBODIMENTS

The technique according to the invention provides a map of cariogenic activity on teeth surfaces by enabling growth of cariogenic microorganisms on a solid replica substrate following incubation in a selective growth medium. The substrate is developed to indicate the extent and locus of cariogenic activity.

According to the invention an examination is performed by contacting the surface to be examined with the substrate. When examining the interior of the mouth, the individual teeth, either separately or as a group, are brought into contact with the substrate to transfer cariogenic bacteria from the teeth to the substrate. Known cariogenic bacteria include *Streptococcus mutans, mitis, sanguis, Actinomyces Israeli, viscosus*, and certain lactobacilli. Any technique for transferring the bacteria may obviously be used.

By way of example, a patient may be made to bite on a chewing gum substrate which molds to the configuration of the teeth. The chewing gum itself is also essentially free of antibacterial agents so as to allow the growth of the cariogenic bacteria thereon. In addition to chewing gum, other substrates are quite obviously possible such as, for example, plant or vegetable gum, alginate, a paper card, a plaster mold, wax, silicone, cellophana, etc. The solid replica substrate surface contains at least one component which is essential for subsequent bacterial growth, such as a main carbon source. The carbon source may be, for example, sucrose, galactose, sorbitol, glucose or other sugars, amino acids, sulphates, or alternatively phosphates and ammonium salts. Absence of this at least one essential component limits bacterial growth anywhere other than in contact with the substrate surface, after removal of the substrate.

After contact between the substrate and the teeth has taken place, the replica substrate is separated from the teeth and washed to remove non-bound cells which might interfere with the localization technique. The replica is then placed into a liquid selective growth medium which contains all of the components necessary for growth of cariogenic bacteria, except one essential component which is provided within the solid replica. Thus, if the replica contains the carbon source, it is absent from the liquid growth medium. Since the other necessary components for growth are present in the liquid medium, growth occurs primarily at the solid-liquid interface.

Other ingredients necessary for proper growth of the cariogenic bacteria are peptides, amino acids, plant and animal extracts, and phosphate. These substances are present in the liquid growth medium.

In addition to containing growth agents, the liquid growth medium or solid substrate may additionally contain components which inhibit the growth of non-cariogenic bacteria. Such materials include, by way of example, potassium tellurite, trypan blue, gentian violet, etc. Likewise the pH of the liquid may also be adjusted to a sufficiently low level as an alternative or cumulative means of inhibiting growth of non-cariogenic bacteria.

An indicator substance is further included, preferably in the liquid growth medium, which is absorbed by the bacteria during their growth. By way of example, such an indicator my include gentian violet. This indicator allows for visualization of the cariogenic activity at its locus. Gentian violet thus serves not only as an indicator, but also as an inhibitor of non-cariogenic bacteria.

Incubation of the solid replica substrate within the liquid medium occurs at temperatures of approximately 35°-37° C. for periods of approximately 6-24 hours sufficient to allow for significant bacterial growth to permit ultimate visualization.

Following incubation of the solid replica within the liquid medium bacterial growth can be easily perceived by absorption of the indicator at certain locations on the replica substrate. This in turn can be correlated with the cariogenic activity of the tooth surface.

Another indication technique which is possible, includes the use of standard immunological reagents which make visualization possible. Such techniques may, for example, include incubating the substrate in an immune serum which contains antibodies which specifically bind with cariogenic bacteria during incubation of the solid replica substrate. If the antibodies are labelled, such as with a chromogenic enzyme, for example, visualization is then possible by subsequently contacting the enzyme with a corresponding substrate. Alternatively, the antibodies may be unlabelled, with the visualization technique including contacting the substrate with a solution of labelled anti-immunoglobulin antibodies which bind to the unlabelled antibodies on the substrate.

EXAMPLE

The process will now be exemplified by way of the following non-limiting example:

The patient is asked to bite down on a solid replica substrate such that a visual imprint of the tooth surface on the chewing gum is made. The gum has the following composition: 20% Paloya gum base (L. A. Dreyfus Co.), 1% glycerol, 60% sucrose, and 19% glucose. The chewing gum may be exposed on only one of its surfaces to the teeth, or may be exposed on both surfaces to the upper and lower teeth. Also, the buceal and lingual sides of the teeth may be exposed.

The chewing gum is then carefully removed from the mouth of the patient, washed briefly in tap water, and exposed to a liquid medium having the following composition: 10 g/l Bactotryptose, 10 g/l proteuse peptone, 75 mg./l trypan blue, 0.8 mg/l gentian violet and 10 ug/l potassium tellurite. The chewing gum is permitted to incubate within the liquid medium for approximately 6-12 hours at a temperature of approximately 37 degrees Centigrade. After incubation, the liquid medium is drained, and the substrate is visually examined for evidence of cariogenically-related microorganisms, which organisms have absorbed the visually-observable dye.

The patient, technician or dentist is then able to identify the locus of the cariogenic activity by correlating the replica with the teeth of the patient.

Thus, although previous techniques have allowed for procedures which merely test for the presence of cariogenic activity, such techniques have not allowed for the localization of the activity and have thus given little more than evidence that a cavity is about to occur. This information would then require the more careful routine examinations which have been traditionally performed and which suffer from the drawbacks mentioned above. Using the technique of the invention the site of the activity is localized and the bacteria may be treated at an early stage using techniques which are now becoming available. Also, the technique involves inexpensive materials which are harmless, unlike x-rays, and does not require peripheral equipment, other than an incubator.

Although the invention has been described with reference to particular means, materials and embodiments, it is to be understood that the invention is not limited to the particulars described and extends to all equivalents. For example, although the invention has been described with reference to chewing gum as the replica substrate, it is clear that other substrates such as cardboard sheets, plaster molds, and the like may be used without going beyond the scope of the invention. Likewise, although the invention has been described with respect to a particular nutrient source in the substrate, it is clear that other nutrient growth sources may be present in either the substrate or the liquid medium to achieve the desired objectives. Finally, although described with reference specifically to tooth examination, it is clear that the localization concept of the invention is not limited to teeth and may be used wherever one desires to determine and localize the existence of suspected bacteria on a surface.

What is claimed is:

1. A method for detecting the presence, extent and location of a specified microorganism on a surface, comprising:
   (a) contacting the surface with a solid substrate containing at least one substance essential for the growth of the specified microorganism;
   (b) removing said solid substrate from the surface and immersing it in a liquid growth medium lacking said at least one substance essential for the growth of the specified microorganism but otherwise having the necessary growth ingredients for growing the specified microorganism; and
   (c) incubating said liquid growth medium with the solid substrate immersed therein to promote the growth of the specified microorganism at the interface between the solid substrate and the liquid medium.

2. The method according to claim 1, wherein: said surface is a subject's teeth, the solid substrate is an impressionable material applied to the subject's teeth, and said specified microorganism is caries-associated bacteria.

3. The method according to claim 2, wherein said impressionable material is chewing gum.

4. The method according to claim 1, including the further step of rinsing the solid substrate with water before immersing it in the liquid growth medium in order to remove non-adherent substances and microorganisms.

5. The method according to claim 1, wherein said at least one substance essential for the growth of the specified microorganism contained in the solid substrate, but lacking in said liquid growth medium, is a carbon source.

6. The method according to claim 5, wherein said carbon source is sucrose.

7. The method according to claim 1, wherein said liquid growth medium includes at least one indicator substance which becomes associated with the microorganism during the incubation of the substrate in the liquid growth medium, to facilitate identification of the specified microorganism.

8. The method according to claim 7, wherein said at least one indicator substance in the liquid growth medium is a chromogenic selective agent absorbed by the microorganism during the incubation of the substrate in the liquid growth medium, to facilitate visual observation.

9. The method according to claim 7, wherein said at least one indicator substance is an immune serum containing fluorescent or enzyme-containing antibodies associated with the specified microorganism during incubation of the substrate in the liquid growth medium.

10. The method according to claim 1, wherein said solid substrate further includes a substance inhibiting the growth of microorganisms except the specified microorganism.

11. The method according to claim 1, wherein said liquid growth medium includes a substance inhibiting the growth of microorganisms except the specified microorganism.

12. A method for detecting the presence of one or more specified microorganisms in an examined medium comprising:

(a) effecting contact between said examined medium and a solid substrate containing at least one substance essential for the growth of the specified microorganism;

(b) immersing said solid substrate in a liquid growth medium lacking said at least one substance essential for the growth of the specified microorganism but otherwise having the necessary growth ingredients for growing the specified microorganism; and (c) incubating said liquid growth medium with the solid substrate immersed therein to promote the growth of the specified microorganism at the interface between the solid substrate and the liquid medium.

13. The method according to claim 12, wherein: said solid substrate is an impressionable material, and said specified microorganism is caries-associated bacteria.

14. The method according to claim 13, wherein said impressionable material is chewing gum.

15. The method according to claim 12, including the further step of rinsing the solid substrate with water before immersing it in the liquid growth medium in order to remove non-adherent substances and microorganisms.

16. The method according to claim 12, wherein said at least one substance essential for the growth of the specified microorganism contained in the solid substrate, but lacking in said liquid growth medium, is a carbon source.

17. The method according to claim 16, wherein said carbon source is sucrose.

18. The method according to claim 12, wherein said solid substrate further includes a substance inhibiting the growth of microorganisms except the specified microorganism.

19. The method according to claim 12, wherein said liquid growth medium includes a substance inhibiting the growth of microorganisms except the specified microorganism.

* * * * *